United States Patent
Johnston, Jr. et al.

(10) Patent No.: US 10,034,697 B2
(45) Date of Patent: Jul. 31, 2018

(54) DETACHABLE ACTUATOR ARM FOR DISTRACTION DEVICES

(71) Applicants: Thomas S. Johnston, Jr., Jacksonville, FL (US); Klaus Kohler, Mulheim (DE)

(72) Inventors: Thomas S. Johnston, Jr., Jacksonville, FL (US); Klaus Kohler, Mulheim (DE)

(73) Assignee: KLS-MARTIN, L.P., Jacksonville, FL (US)

( * ) Notice: Subject to any disclaimer, the term of this patent is extended or adjusted under 35 U.S.C. 154(b) by 511 days.

(21) Appl. No.: 14/933,494

(22) Filed: Nov. 5, 2015

(65) Prior Publication Data

US 2016/0120580 A1    May 5, 2016

Related U.S. Application Data

(60) Provisional application No. 62/075,538, filed on Nov. 5, 2014.

(51) Int. Cl.
    *A61B 17/66*     (2006.01)
    *A61B 17/80*     (2006.01)
    *A61B 17/68*     (2006.01)

(52) U.S. Cl.
CPC ........ *A61B 17/8019* (2013.01); *A61B 17/663* (2013.01); *A61B 2017/681* (2013.01)

(58) Field of Classification Search
CPC ..... A61B 17/66; A61B 17/663; A61B 17/666; A61B 17/8004; A61B 17/8019; A61B 2017/681
See application file for complete search history.

(56) References Cited

U.S. PATENT DOCUMENTS

| | | | | |
|---|---|---|---|---|
| 5,769,850 A * | 6/1998 | Chin | ............ | A61B 17/171 606/102 |
| 5,846,245 A * | 12/1998 | McCarthy | ...... | A61B 17/6416 606/105 |
| 5,855,580 A * | 1/1999 | Kreidler | ........ | A61B 17/663 606/282 |
| 5,893,879 A * | 4/1999 | Hirshowitz | ...... | A61B 17/08 606/213 |
| 5,895,387 A * | 4/1999 | Guerrero | ........ | A61B 17/6433 606/281 |
| 6,277,124 B1 * | 8/2001 | Haag | .......... | A61B 17/663 606/105 |
| 6,423,069 B1 * | 7/2002 | Sellers | .......... | A61B 17/663 606/105 |
| 6,673,079 B1 * | 1/2004 | Kane | ............ | A61B 17/663 606/105 |
| 6,752,808 B2 * | 6/2004 | Schumacher | ..... | A61B 17/663 606/90 |
| 6,786,910 B2 * | 9/2004 | Cohen | .......... | A61B 17/66 606/71 |
| 6,884,243 B2 * | 4/2005 | Sellers | .......... | A61B 17/663 606/105 |
| 6,908,469 B2 * | 6/2005 | Sellers | .......... | A61B 17/663 606/105 |
| 6,972,020 B1 * | 12/2005 | Grayson | ....... | A61B 17/663 606/90 |

(Continued)

*Primary Examiner* — Eric S Gibson
(74) *Attorney, Agent, or Firm* — Thomas C. Saitta

(57) ABSTRACT

A detachable actuator arm as part of or in combination with an osteogenesis distractor device, the actuator arm being detachable from the distraction mechanism of the distractor device by manipulation of a proximally disposed release mechanism.

20 Claims, 3 Drawing Sheets

(56) References Cited

U.S. PATENT DOCUMENTS

| | | | | |
|---|---|---|---|---|
| 7,771,434 B2* | 8/2010 | Johnston | | A61B 17/663 606/105 |
| 7,875,033 B2* | 1/2011 | Richter | | A61B 17/66 606/280 |
| 8,808,290 B2* | 8/2014 | Dubois | | A61B 17/663 606/58 |
| 8,858,566 B2* | 10/2014 | Noon | | A61B 17/663 606/105 |
| 9,308,026 B2* | 4/2016 | Ruiz | | A61B 17/663 |
| 9,622,782 B1* | 4/2017 | Alruhaimi | | A61B 17/666 |
| 9,622,801 B1* | 4/2017 | Alruhaimi | | A61B 17/8019 |
| 9,649,132 B1* | 5/2017 | Linck | | A61B 17/663 |
| 9,700,353 B2* | 7/2017 | Harris | | A61B 17/663 |
| 9,782,202 B2* | 10/2017 | Knoepfle | | A61B 17/66 |
| 2002/0116002 A1* | 8/2002 | Sellers | | A61B 17/663 606/71 |
| 2002/0156485 A1* | 10/2002 | Sellers | | A61B 17/663 606/105 |
| 2005/0119659 A1* | 6/2005 | Pfefferle | | A61B 17/663 606/71 |
| 2005/0256526 A1* | 11/2005 | Johnston | | A61B 17/663 606/282 |
| 2006/0015118 A1* | 1/2006 | Richter | | A61B 17/66 606/90 |
| 2006/0079902 A1* | 4/2006 | Johnston | | A61B 17/663 606/71 |
| 2007/0043370 A1* | 2/2007 | Ueda | | A61B 17/663 606/71 |
| 2007/0162045 A1* | 7/2007 | Ahmad | | A61B 17/663 606/105 |
| 2008/0039861 A1* | 2/2008 | Ahmad | | A61B 17/1637 606/105 |
| 2009/0036892 A1* | 2/2009 | Karidis | | A61B 17/62 606/60 |
| 2009/0088766 A1* | 4/2009 | Magill | | A61B 17/663 606/90 |
| 2010/0152734 A1* | 6/2010 | Mulone | | A61B 17/663 606/60 |
| 2011/0125162 A1* | 5/2011 | Noon | | A61B 17/663 606/105 |
| 2012/0277749 A1* | 11/2012 | Mootien | | A61B 17/663 606/70 |
| 2012/0316561 A1* | 12/2012 | Dubois | | A61B 17/663 606/58 |
| 2013/0310880 A1* | 11/2013 | Ruiz | | A61B 17/663 606/282 |
| 2014/0163576 A1* | 6/2014 | Knoepfle | | A61B 17/663 606/105 |
| 2015/0173814 A1* | 6/2015 | Gerhardt | | A61B 17/663 606/282 |
| 2016/0120580 A1* | 5/2016 | Johnston, Jr. | | A61B 17/8019 606/282 |
| 2016/0183989 A1* | 6/2016 | Kubis | | A61B 17/8071 606/281 |

* cited by examiner

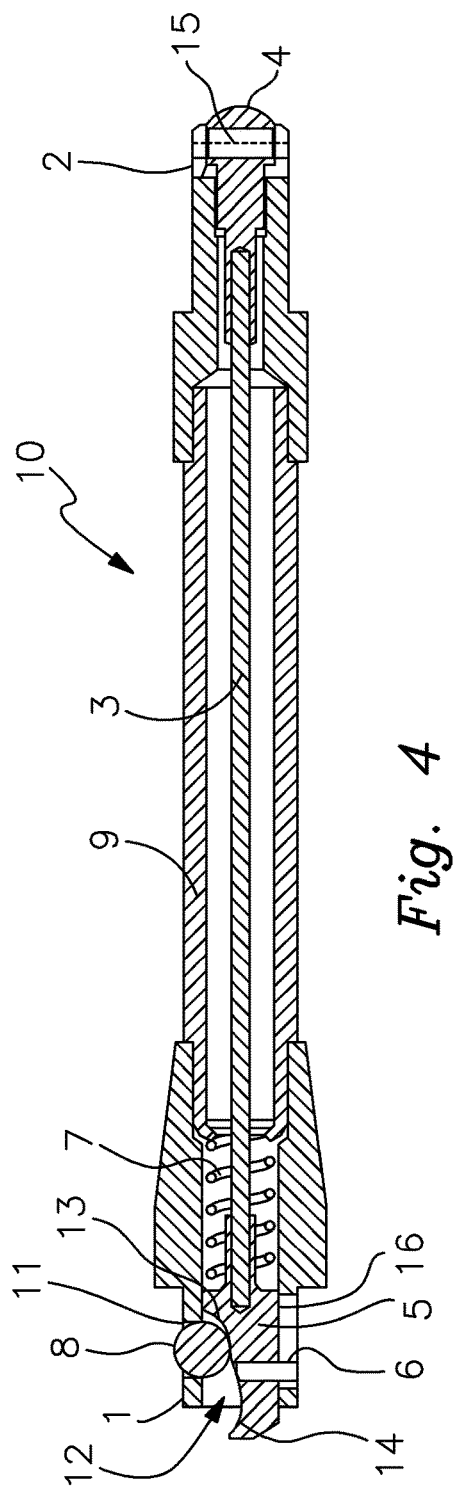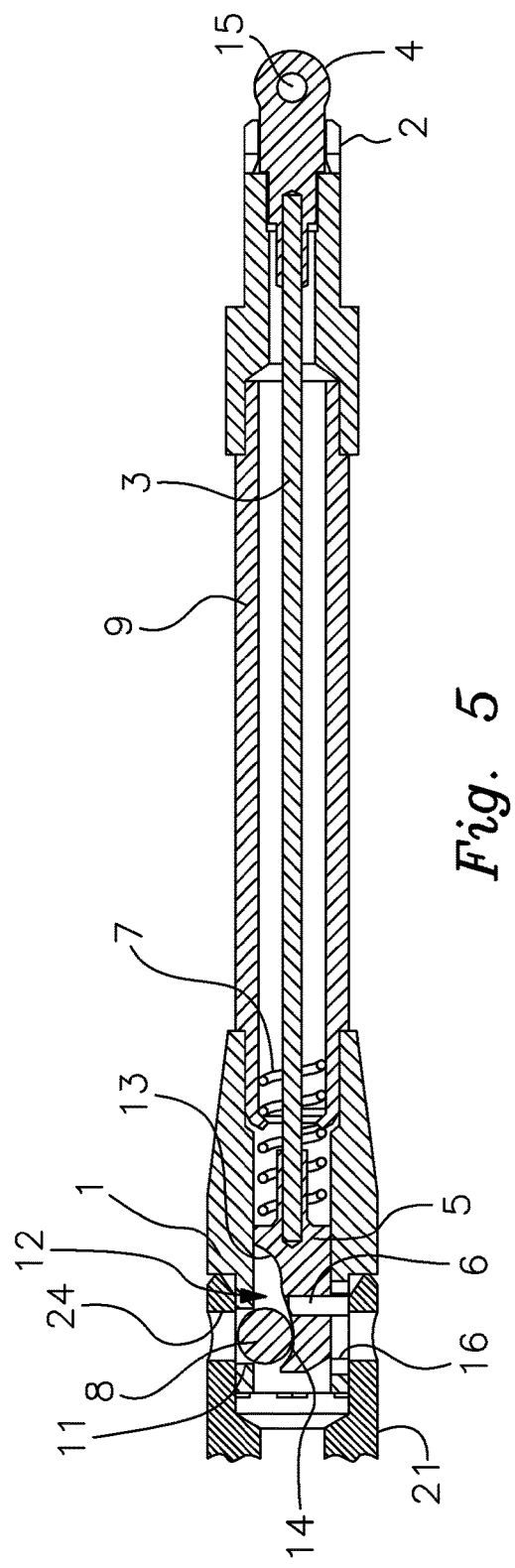

DETACHABLE ACTUATOR ARM FOR DISTRACTION DEVICES

This application claims the benefit of U.S. Provisional Patent Application Ser. No. 62/075,538, filed Nov. 5, 2014.

BACKGROUND OF THE INVENTION

This invention relates generally to the field of medical compression and distraction devices in the field of bone fixation, repair and regeneration, and more particularly relates to such devices and methods utilized in osteogenesis, such as with maxillary craniofacial repair, facial or cranial reconstruction, or treatment for congenital, developmental and traumatic defects.

It is often desirable or necessary to effect reconstruction or repair of the craniofacial bones defining the face or cranium of a person, such as for example the midface, the mandible and/or the maxilla. This need may arise from congenital conditions, developmental disorders or trauma. In many circumstances the abnormalities are corrected by first performing an osteotomy, i.e., cutting or fracturing a bone to create two segments separated by a gap or space. In some instances the bone segments will be shifted into the proper orientation and alignment, and then fixed in place relative to each other until bone growth across the gap (osteogenesis) results in the formation of a unitary bone member. In other instances it is necessary to lengthen the original bone member, in which case after the osteotomy devices known as distractors are utilized to incrementally lengthen the bone.

A distractor is a device that has affixation members, such as bone plates, that are joined to each of the bone segments on opposite sides of the osteotomy. The device further includes a distraction mechanism, such as a rotatable threaded rod for example, that enables the distance between the bone plates to be slowly increased over time, thereby allowing new bone growth to occur between the bone segments. The new bone growth increases in dimension until the proper bone length is achieved, at which time the distraction process is halted and the distractor is removed after sufficient healing time. The distraction mechanism is usually actuated by a separate tool, such as a screw-driver like hand tool having a polygonal socket which mates with an exposed polygonal tip on the proximal end of the distractor (the end most accessible to the surgeon) or a polygonal tip which mates with an exposed polygonal socket on the proximal end of the distractor. The osteogenesis process comprises separating the bone plates a short distance, allowing bone growth to fill in the gap, separating the bone plates a short distance again, allowing the bone growth to occur, etc., with the process repeated until the desired bone configuration is achieved.

As a typical example, it is often desired to advance the midface or maxillary region relative to the jaw and skull to correct for maxillary hypoplasia, where the upper lip and/or nose are depressed relative to the remainder of the face structure. In this case the osteotomy may be performed across the maxilla to the nasal cavity, and a pair of distractors is affixed across the osteotomy gap by attaching bone plates to the bone segments with mechanical fasteners. Gradual incremental extension of the distractors, i.e., separation of the bone plates, advances the anterior maxillary segment relative to the posterior maxillary segments while bone regeneration fills in the osteotomy gap. When the proper position is achieved, distraction is halted. After sufficient regeneration and healing, the distractors are removed.

Because the distractors are typically positioned within or covered by tissue, it is often necessary to elongate the main body of the distractor in the proximal direction or alternatively to connect an extension actuator arm to the distraction mechanism that is exposed and easily accessible to the doctor, surgeon or technician when the device needs to be actuated. Providing an elongated main body is not an optimal solution, as the distraction device must remain in the patient until healing as completed and the extended portion now serves no function. Known extension arms are not optimal either, as the mechanism for attachment and detachment of the extension arm from the main body is usually covered by tissue, such that dissection of tissue is required to expose the detachment mechanism in order to remove the arm after the distraction process has been completed but before the distraction device may be removed from the patient.

It is an object of this invention to provide a releasable and removable actuator arm, primarily for a craniofacial maxillary type distraction device, whereby the actuator arm may be easily and rapidly released and removed from the patient once final distraction has occurred, such that only the distractor operative mechanism and bone plates remain in the patient during the healing process, wherein the actuator arm is releasable from the proximal end.

SUMMARY OF THE INVENTION

A detachable actuator arm is provided as part of an osteogenesis distractor device or in combination with an osteogenesis distraction device, the actuator arm being structured such that its proximal end is configured to mate with a drive tool such that the arm may be rotated when needed, with the distal end of the arm being structured such that the arm is mated in lockable manner with the operative distraction mechanism of the distractor main body. Rotation of the actuator arm results in rotation of the distraction mechanism of the distraction device and separation of the bone plates affixed to the bone segments. The mechanism for detaching the actuator arm from the distractor device is positioned on the proximal end of the actuator arm such that it is exposed and readily accessible, thereby enabling the actuator arm to be detached from the distraction mechanism when the distraction process is complete.

In the preferred embodiment the actuator arm is detachably connected to the distraction mechanism using a detent ball, a portion of which in the operative or locked status extends radially outward from the male distal end of the arm and seats within a channel, opening or recess internally disposed in the female receiving end of the distraction mechanism, thereby attaching the actuator arm to the distraction mechanism of the distractor device such that rotation of the actuator arm results in rotation of the distraction mechanism to separate the bone plates. The actuator arm is tubular, such that an internal shaft, rod or wire member extends from a distal head positioned within the distal end of the arm to a proximal head positioned substantially within the proximal end of the arm. The distal head comprises a multi-level or sloping contact surface that abuts the detent ball, the contact surface having a distal portion or recess that is deeper than a proximal portion or recess. The proximal head comprises a structure that is manipulated in order to detach the arm from the distraction mechanism, such as a projection or a transverse bore or recess that may be gripped or hooked and then pulled in the proximal direction. During the operative status when distraction is being performed, the shallow proximal recess abuts the interior side of the detent ball to hold the ball in the extended position such that the arm is locked to the distraction mechanism. To detach the arm from the distraction mechanism, the proximal head is grasped and pulled, thereby moving the distal head in the proximal direction such that the deeper distal recess is aligned with the detent ball such that the ball recedes into the distal end of the arm and no longer secures the arm to the distraction mechanism.

In alternative format, the invention is a detachable actuator arm in combination with a distractor device comprising a distractor device comprising a main body, bone plates and a distraction mechanism which upon actuation separates said bone plates, said distraction mechanism comprising an internal recess; a detachable actuator arm adapted to releasably connect with said distraction mechanism, said actuator arm comprising an elongated tubular main body having a distal end and a proximal end, and a distal head and a proximal head connected together by an internal member, wherein said distal head, said proximal head and said internal member are disposed within said main body and are axially movable within said main body, and wherein said distal end comprises a side opening; said distal head comprising a contact surface having a distal recess and a proximal recess, said distal recess being deeper than said proximal recess; a spring member biasing said distal head, said proximal head and said internal member in the distal direction within said main body; a detent ball disposed within said distal end between said opening and said proximal recess of said contact surface, wherein in a locked position a portion of said detent ball extends through said opening into said recess of said distraction mechanism, thereby locking said distal end of said actuator arm to said distraction mechanism; and wherein said distal head is movable in the proximal direction into a release position by pulling said proximal head in the proximal direction relative to said main body, thereby aligning said distal recess with said detent ball such that said detent ball does not extend through said opening into said internal recess of said distraction mechanism and said actuator arm is detachable from said distraction mechanism. Furthermore, such invention may be defined wherein said proximal head when disposed in the release position is precluded from movement in the distal direction; wherein said internal member is a rigid member; wherein said internal member is a flexible member; wherein said proximal head comprises a transverse bore and said transverse bore is positioned externally to said proximal end of said actuator arm; wherein said main body of said actuator arm comprises a pivoting member; and/or wherein said distal head comprises a pin and said distal end comprises a slot, such that said pin extends into said slot to preclude rotation of said distal head relative to said distal end.

Alternatively, the invention is a detachable actuator arm in combination with a distractor device comprising a distractor device comprising a main body, bone plates and a distraction mechanism which upon rotational actuation separates said bone plates, said distraction mechanism comprising a polygonal socket having an internal recess; a detachable actuator arm adapted to releasably connect with said distraction mechanism, said actuator arm comprising an elongated tubular main body having a distal end and a proximal end, said distal end being structured to mate with said polygonal socket of said distraction mechanism and comprising a side opening; said actuator arm further comprising a distal head and a proximal head connected together by an internal member, wherein said distal head, said proximal head and said internal member are disposed internally to said main body and are axially movable within said main body, and wherein a portion of said proximal head extends from said proximal end of said actuator arm; said distal head comprising a sloping contact surface, wherein relative to said side opening said contact surface slopes upward in the proximal direction; a spring member biasing said distal head, said proximal head and said internal member in the distal direction within said main body; a detent ball disposed within said distal end between said opening and said contact surface, wherein in a locked position said contact surface extends a portion of said detent ball through said side opening and into said internal recess of said distraction mechanism, thereby locking said distal end of said actuator arm to said distraction mechanism; and wherein said distal head is movable in the proximal direction into a release position by pulling said proximal head in the proximal direction relative to said main body, thereby moving said contact surface in the proximal direction such that said detent ball is not extended through said side opening into said internal recess of said distraction mechanism and said actuator arm is detachable from said distraction mechanism. Furthermore, such invention may be defined wherein said contact surface comprises a distal recess and a proximal recess, said distal recess being deeper than said proximal recess; wherein said proximal head when disposed in the release position is precluded from movement in the distal direction; wherein said internal member is a rigid member; wherein said internal member is a flexible member; wherein said proximal head comprises a transverse bore and said transverse bore is positioned externally to said proximal end of said actuator arm; wherein said main body of said actuator arm comprises a pivoting member; and/or wherein said distal head comprises a pin and said distal end comprises a slot, such that said pin extends into said slot to preclude rotation of said distal head relative to said distal end.

Still alternatively, the invention is a detachable actuator arm in combination with a distractor device comprising a distractor device comprising a main body, bone plates and a distraction mechanism which upon rotational actuation separates said bone plates, said distraction mechanism comprising a polygonal socket having an internal recess; a detachable actuator arm adapted to releasably connect with said distraction mechanism, said actuator arm comprising an elongated tubular main body having a distal end and a proximal end, said distal end being structured to mate with said polygonal socket of said distraction mechanism and comprising a side opening; said actuator arm further comprising a distal head and a proximal head connected together by an internal member, wherein said distal head, said proximal head and said internal member are disposed internally to said main body and are axially movable within said main body, and wherein a portion of said proximal head extends from said proximal end of said actuator arm; said distal head comprising a contact surface having a distal recess and a proximal recess, wherein relative to said side opening said distal recess is deeper than said proximal recess, and wherein said distal head comprises a pin and said distal end comprises a slot, such that said pin extends into said slot to preclude rotation of said distal head relative to said distal end; a spring member biasing said distal head, said proximal head and said internal member in the distal direction within said main body; a detent ball disposed within said distal end between said opening and said proximal recess of said contact surface, wherein in a locked position said contact surface extends a portion of said detent ball through said side opening and into said internal recess of said distraction mechanism, thereby locking said distal end of said actuator arm to said distraction mechanism; wherein said distal head is movable in the proximal direction into a release position by pulling said proximal head in the proximal direction relative to said main body, thereby moving said contact surface in the proximal direction such that said distal recess is aligned with said detent ball and said detent ball is not extended through said side opening into said internal recess of said distraction mechanism and said actuator arm is detachable from said distraction mechanism; and wherein with said proximal head disposed in the release position said proximal head is precluded from movement in the distal direction. Furthermore, such invention defined wherein said internal member is a rigid member; wherein said internal member is a flexible member; wherein said proximal head comprises a transverse bore and said transverse bore is positioned externally to said proximal end of said actuator arm; and/or wherein said main body of said actuator arm comprises a pivoting member.

BRIEF DESCRIPTION OF THE DRAWINGS

FIG. 4 is a longitudinal cross-sectional view of the embodiment of FIG. 1, shown in the locked status.

FIG. 5 is a longitudinal cross-sectional view of the embodiment of FIG. 2, shown in the released status and not yet detached from a distractor mechanism.

DETAILED DESCRIPTION OF THE INVENTION

Figure 1:
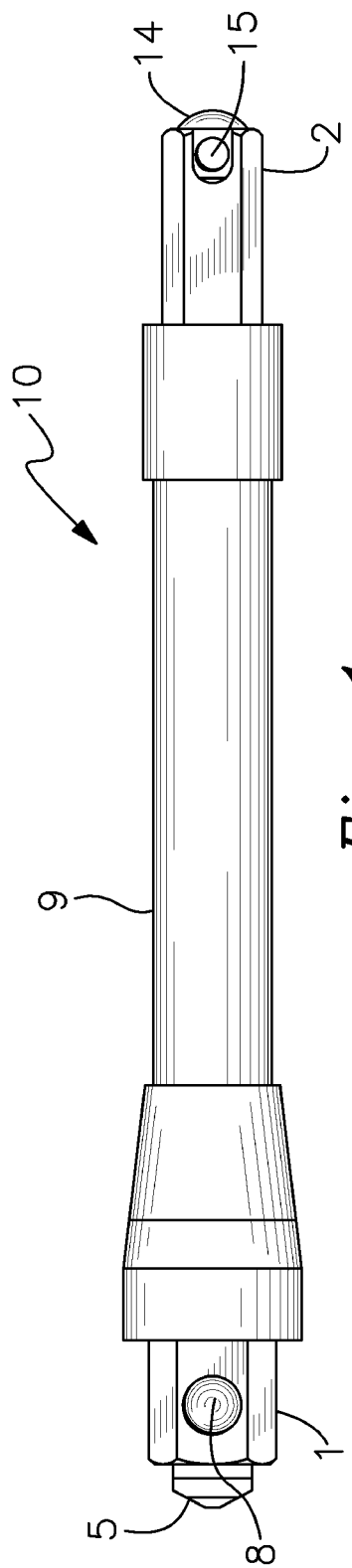
FIG. 1 is a view of an embodiment of the actuator arm, shown in the locked status.

The invention is a detachable actuator arm that is utilized as part of or in combination with a craniofacial maxillary or similar osteogenesis distraction device, the distraction device comprising an operative distraction mechanism and bone plates for affixation to bone segments, whereby rotation of the actuator arm initiates the distraction mechanism and separates the bone plates. Such distraction devices are well known in the art and the operative distraction mechanisms are well understood. Representative examples of typical craniofacial maxillary distraction devices are shown for example in U.S. Pat. Nos. 5,855,580, 6,471,706, 7,686,836 and 7,771,434, the disclosures of which are incorporated herein by reference.

As used herein, the term "proximal" shall refer to the direction toward the exterior of the patient, i.e., the direction toward the surgeon, doctor or technician that operates the distractor device, or the end of the distractor device or the actuator arm that is most accessible and comprises the structure that mates with the drive tool. The term "distal" therefore refers to the opposite direction, i.e., the direction away from the surgeon, doctor or technician that operates the distractor device, or the farther end of the distractor device or the actuator arm that is least accessible and is typically covered by tissue during the distraction process.

The actuator arm 10 comprises an elongated, tubular main body 9 having a distal end 1 and a proximal end 2. The main body 9 may be constructed as a rigid member or as a flexible member depending on the choice of materials and design. At least a portion of the proximal end 2 has a male cross-sectional shape, typically polygonal or non-cylindrical, configured to mate with a corresponding female socket or recess on a separate driver tool, whereby the actuator arm 10 may be rotated about its longitudinal axis by temporarily connecting the driver tool to the proximal end 2 of the actuator arm 10 and rotating the tool. At least a portion of the distal end 1 of the arm 10 has a male cross-sectional shape, typically polygonal or non-cylindrical, configured to mate with a corresponding female socket or recess on the proximal end of the operative distraction mechanism 21 of the main body 22 of the distractor device 20, whereby rotation of the arm 10 results in operation of the operative distraction mechanism 21 to cause separation of the bone plates 23 affixed to the bone segments. This distal mating mechanism is structured such that the actuator arm 10 remains affixed or locked to the distraction mechanism 21 until after the distraction process has been completed.

Figure 3:
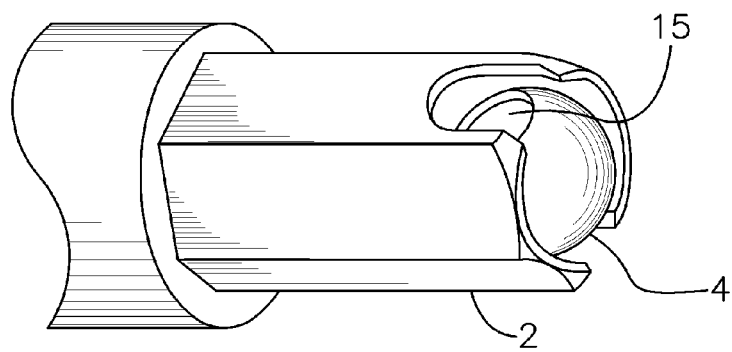
FIG. 3 is a partial view of distal end of the embodiment of FIG. 1, shown in the locked status.

The actuator arm 10 further comprises an elongated internal member 3 in the form of a shaft, wire, rod, etc., a distal head 5 connected to the distal end of the internal member 3 and positioned within the distal end 1 of the arm 10, and a proximal head 4 connected to the proximal end of the internal member 3 and positioned within the proximal end 2 of the arm 10. The internal member 3, distal head 5 and proximal head 4 are retained within the main body 9, distal end 1 and proximal end 2 in a manner that allows movement of the internal member 3, distal head 5 and proximal head 4 in the axial direction relative to the main body 9, distal end 1 and proximal end 2 of the actuator arm 10. An internal spring member 7, preferably a coiled spring disposed toward the distal end 1 of the arm 10 and abutting the distal head 5, is retained within the arm 10 such that the internal member 3, distal head 5 and proximal head 4 are biased toward the distal end 1 of the arm 10 when the arm 10 is in the operative locked status, i.e., when the arm 10 is connected to the distraction mechanism 21 and the distraction process is ongoing, as shown in FIGS. 1, 3 and 4.

The actuator arm 10 is detachably connected to the distraction mechanism 21 by a detachment mechanism. As shown, the preferable embodiment for the detachment mechanism comprises a detent ball 8 retained within the distal end 1 of the arm 10. The distal end 1 of the actuator arm 10 is provided with a side opening 11 that allows a portion of the detent ball 8 to extend radially or transversely outward from the male distal end 1 of the arm 10 when in the locked status, such that the detent ball 8 seats within an internal, annular channel or recess 24 disposed within the proximal female receiving end of the distraction mechanism 21. The proximal head 4 comprises a multi-level or sloping cam-like contact surface 12 that abuts the interior side of the detent ball 8, the contact surface 12 preferably having a distal recess or shoulder 13 that is deeper than a proximal recess or shoulder 14 in order to better secure the detent ball 8.

Figure 2:
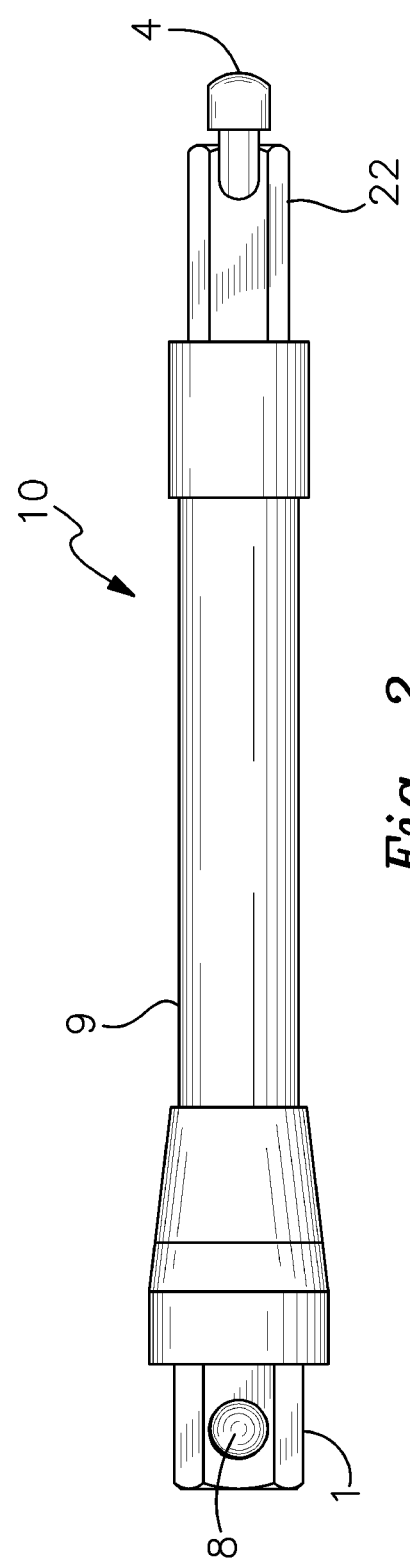
FIG. 2 is a view of the embodiment of FIG. 1, shown in the released status.

The proximal head 4 is positioned within the tubular main body 9 such that a portion of the proximal head 4 is exposed at or extends beyond the proximal end 2 of the main body 9. This proximal portion of the proximal head 9 comprises an exposed release member or structure 15 that may be gripped, hooked or otherwise secured and pulled by a separate release tool, such as a hook, forceps, etc. As shown in the drawings, the release member 15 may comprise a bore or recess transversely positioned in the proximal end of the proximal head 4. In the locked status the relatively shallow proximal recess 14 of the distal head 5 abuts the interior side of the detent ball 8, maintaining the detent ball 8 in the extended position with a portion of the ball 8 residing in the internal channel 24 of the distraction mechanism 21 such that actuator arm 10 cannot be axially removed from the distraction mechanism 21. To detach the arm 10 from the distraction mechanism 21, the proximal head 4 is grasped or hooked and pulled in the proximal direction, thereby compressing spring 7 and moving the deeper distal recess 13 into alignment with the interior side of the detent ball 8 such that the ball 8 is free to move into the distal end 1 of the arm and therefore no longer secures the arm 10 to the distraction mechanism 21, as shown in FIGS. 2 and 5. The actuator arm 10 is now detachable from the distraction mechanism 21 simply by linear movement in the axial direction.

The distal head 5 is preferably provided with a mechanism to prevent axial rotation of the distal head 5 within the distal end 1, thereby insuring that the contact surface 12 is always properly oriented relative to the detent ball 8 and opening 11. As shown in the drawings, this may be accomplished by providing a post or pin 6 that extends into an anti-rotation slot 16 disposed in side of the distal end 1 of the arm actuator 10.

In a preferred embodiment, the actuator arm 10 is structured such that upon the proximal head 4 being proximally moved relative to the proximal end 2 of the arm 10, the proximal head 4 may be secured or retained in the release position with the release tool removed from the actuator arm 10. In the embodiment shown in the drawings, this release locking mechanism has both the bore at the proximal end 2 the actuator arm 10 and the portion of the proximal head 4 received therein being structured with generally rectangular cross-sections, such that upon full retraction of the proximal head 4 it may be rotated such that the proximal head 4 is not able to be pulled back into the bore by the spring 7. This allows the actuator arm 10 to be more easily manipulated to separate it from the distraction mechanism 21. Other non-circular configurations or configurations with keys and slots may also be utilized to secure the proximal head 4 in the released position.

Figure 6:
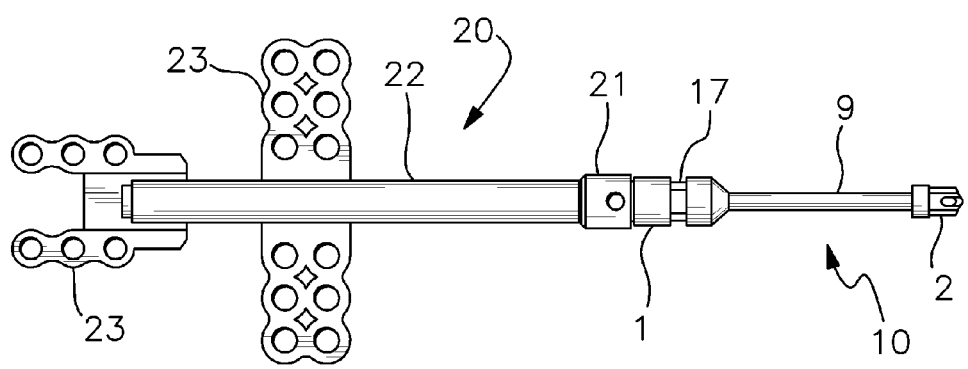
FIG. 6 is a view of an alternative embodiment of the actuator arm having a pivoting connection and shown connected to a representative distractor mechanism.

In addition to structuring the elongated main body 9 so as to be either rigid or flexible, the main body 9 may be provided with a pivoting mechanism 17, such as a hinge, swivel or the like, such that the angle of the proximal portion of the main body 9 may be altered relative to the angle of the distal portion of the main body 9, as shown in FIG. 6. In this embodiment the internal member 3 must be a flexible wire, cable, line or like member.

It is contemplated that equivalents and substitutions for certain elements set forth above may be obvious to those skilled in the art, and therefore the true scope and definition of the invention is to be as set forth in the following claims.

We claim:

1. A detachable actuator arm in combination with a distractor device comprising:
    a distractor device comprising a main body, bone plates and a distraction mechanism which upon actuation separates said bone plates, said distraction mechanism comprising an internal recess;
    a detachable actuator arm adapted to releasably connect with said distraction mechanism, said actuator arm comprising an elongated tubular main body having a distal end and a proximal end, and a distal head and a proximal head connected together by an internal member, wherein said distal head, said proximal head and said internal member are disposed within said main body and are axially movable within said main body, and wherein said distal end comprises a side opening;
    said distal head comprising a contact surface having a distal recess and a proximal recess, said distal recess being deeper than said proximal recess;
    a spring member biasing said distal head, said proximal head and said internal member in a distal direction within said main body;
    a detent ball disposed within said distal end between said opening and said proximal recess of said contact surface, wherein in a locked position a portion of said detent ball extends through said opening into said recess of said distraction mechanism, thereby locking said distal end of said actuator arm to said distraction mechanism;
    and wherein said distal head is movable in a proximal direction into a release position by pulling said proximal head in the proximal direction relative to said main body, thereby aligning said distal recess with said detent ball such that said detent ball does not extend through said opening into said internal recess of said distraction mechanism and said actuator arm is detachable from said distraction mechanism.

2. The combination of claim 1, wherein said proximal head when disposed in the release position is precluded from movement in the distal direction.

3. The combination of claim 1, wherein said internal member is a rigid member.

4. The combination of claim 1, wherein said internal member is a flexible member.

5. The combination of claim 1, wherein said proximal head comprises a transverse bore and said transverse bore is positioned externally to said proximal end of said actuator arm.

6. The combination of claim 1, wherein said main body of said actuator arm comprises a pivoting member.

7. The combination of claim 1, wherein said distal head comprises a pin and said distal end comprises a slot, such that said pin extends into said slot to preclude rotation of said distal head relative to said distal end.

8. A detachable actuator arm in combination with a distractor device comprising:
    a distractor device comprising a main body, bone plates and a distraction mechanism which upon rotational actuation separates said bone plates, said distraction mechanism comprising a polygonal socket having an internal recess;
    a detachable actuator arm adapted to releasably connect with said distraction mechanism, said actuator arm comprising an elongated tubular main body having a distal end and a proximal end, said distal end being structured to mate with said polygonal socket of said distraction mechanism and comprising a side opening;
    said actuator arm further comprising a distal head and a proximal head connected together by an internal member, wherein said distal head, said proximal head and said internal member are disposed internally to said main body and are axially movable within said main body, and wherein a portion of said proximal head extends from said proximal end of said actuator arm;
    said distal head comprising a sloping contact surface, wherein relative to said side opening said contact surface slopes upward in a proximal direction;
    a spring member biasing said distal head, said proximal head and said internal member in a distal direction within said main body;

a detent ball disposed within said distal end between said opening and said contact surface, wherein in a locked position said contact surface extends a portion of said detent ball through said side opening and into said internal recess of said distraction mechanism, thereby locking said distal end of said actuator arm to said distraction mechanism;

and wherein said distal head is movable in the proximal direction into a release position by pulling said proximal head in the proximal direction relative to said main body, thereby moving said contact surface in the proximal direction such that said detent ball is not extended through said side opening into said internal recess of said distraction mechanism and said actuator arm is detachable from said distraction mechanism.

9. The combination of claim 8, wherein said contact surface comprises a distal recess and a proximal recess, said distal recess being deeper than said proximal recess.

10. The combination of claim 8, wherein said proximal head when disposed in the release position is precluded from movement in the distal direction.

11. The combination of claim 8, wherein said internal member is a rigid member.

12. The combination of claim 8, wherein said internal member is a flexible member.

13. The combination of claim 8, wherein said proximal head comprises a transverse bore and said transverse bore is positioned externally to said proximal end of said actuator arm.

14. The combination of claim 8, wherein said main body of said actuator arm comprises a pivoting member.

15. The combination of claim 8, wherein said distal head comprises a pin and said distal end comprises a slot, such that said pin extends into said slot to preclude rotation of said distal head relative to said distal end.

16. A detachable actuator arm in combination with a distractor device comprising:
   a distractor device comprising a main body, bone plates and a distraction mechanism which upon rotational actuation separates said bone plates, said distraction mechanism comprising a polygonal socket having an internal recess;
   a detachable actuator arm adapted to releasably connect with said distraction mechanism, said actuator arm comprising an elongated tubular main body having a distal end and a proximal end, said distal end being structured to mate with said polygonal socket of said distraction mechanism and comprising a side opening;
   said actuator arm further comprising a distal head and a proximal head connected together by an internal member, wherein said distal head, said proximal head and said internal member are disposed internally to said main body and are axially movable within said main body, and wherein a portion of said proximal head extends from said proximal end of said actuator arm;
   said distal head comprising a contact surface having a distal recess and a proximal recess, wherein relative to said side opening said distal recess is deeper than said proximal recess, and wherein said distal head comprises a pin and said distal end comprises a slot, such that said pin extends into said slot to preclude rotation of said distal head relative to said distal end;
   a spring member biasing said distal head, said proximal head and said internal member in a distal direction within said main body;
   a detent ball disposed within said distal end between said opening and said proximal recess of said contact surface, wherein in a locked position said contact surface extends a portion of said detent ball through said side opening and into said internal recess of said distraction mechanism, thereby locking said distal end of said actuator arm to said distraction mechanism;
   wherein said distal head is movable in a proximal direction into a release position by pulling said proximal head in the proximal direction relative to said main body, thereby moving said contact surface in the proximal direction such that said distal recess is aligned with said detent ball and said detent ball is not extended through said side opening into said internal recess of said distraction mechanism and said actuator arm is detachable from said distraction mechanism;
   and wherein with said proximal head disposed in the release position said proximal head is precluded from movement in the distal direction.

17. The combination of claim 16, wherein said internal member is a rigid member.

18. The combination of claim 16, wherein said internal member is a flexible member.

19. The combination of claim 8, wherein said proximal head comprises a transverse bore and said transverse bore is positioned externally to said proximal end of said actuator arm.

20. The combination of claim 16, wherein said main body of said actuator arm comprises a pivoting member.

* * * * *